United States Patent [19]

Yin

[11] Patent Number: 5,001,279

[45] Date of Patent: Mar. 19, 1991

[54] AQUEOUS SYNTHESIS OF 2-HALO-4,6-DINITRORESORCINOL AND 4,6-DIAMINORESORCINOL

[75] Inventor: Tyze-Kuan T. Yin, Concord, Calif.

[73] Assignee: The Dow Chemical Company, Midland, Mich.

[21] Appl. No.: 438,839

[22] Filed: Nov. 17, 1989

[51] Int. Cl.$^5$ ............................................. C07C 205/26
[52] U.S. Cl. .................................... 568/709; 568/712; 568/713
[58] Field of Search ............... 568/704, 712, 713, 765, 568/770, 778, 709, 711

[56] References Cited

U.S. PATENT DOCUMENTS

| | | | |
|---|---|---|---|
| 3,726,929 | 4/1973 | Payne et al. | 568/770 |
| 4,001,340 | 1/1977 | Smith et al. | 568/778 |
| 4,766,244 | 8/1988 | Lysenko et al. | |
| 4,835,306 | 5/1989 | Lysenko | |

Primary Examiner—Werren B. Lone

[57] ABSTRACT

The displacement of halogen from a 1,2,3-trihalo-4,6-dinitroresorcinol can be carried out in an aqueous medium using alkali metal hydroxide to form 2-halo-4,6,-dinitroresorcinol. The product is a useful intermediate in the synthesis of 4,6-diaminoresorcinol, which is a monomer for polybenzoxazole polymers. The process from part of a useful aqueous process for synthesizing 4,6-diaminoresorcinol.

20 Claims, No Drawings

AQUEOUS SYNTHESIS OF 2-HALO-4,6-DINITRORESORCINOL AND 4,6-DIAMINORESORCINOL

BACKGROUND OF THE INVENTION

The present invention relates to the synthesis of 2-halo-4,6-dinitroresorcinol. That compound is a useful intermediate in the synthesis of monomers for making cis-polybenzoxazoles (cis-PBO).

4,6-Diaminoresorcinol and its acid salts are known to be useful monomers in the synthesis of cis-PBO. It is known to synthesize the monomer from 1,2,3-trichlorobenzene in a three-step process by:
(1) nitrating 1,2,3-trichlorobenzene with nitric acid to form 1,2,3-trichloro-4,6-dinitrobenzene;
(2) contacting the product of step (1) with alkali metal hydroxide in an alkanol solution under conditions such that the chlorine atoms in the 1- and 3-positions are displaced to form 2-halo-4,6-dinitroresorcinol; and
(3) contacting the product of step (2) with a hydrogen-reducing agent and a catalyst in an organic solution under conditions such that it is reduced to form 4,6-diaminoresorcinol.

The process is fully described in Lysenko, *High Purity Process for the Preparation of 4,6-Diamino-1,3-benzenediol,* U.S. Pat. No. 4,766,244 (Aug. 23, 1988) which is incorporated herein by reference.

The known process is effective to produce 4,6-diaminoresorcinol in high yields. However, it uses large amounts of organic solvent, which is undesirable for two reasons. First, organic solvents are substantially more expensive than aqueous solvents for commercial scale production. Second, the organic solvents are flammable, which is particularly undesirable in working with the nitrated aromatic intermediates previously described. What is needed is a process to produce 4,6-diaminoresorcinol while reducing or eliminating the organic solvents used in the synthesis.

SUMMARY OF THE INVENTION

One aspect of the present invention is a process for synthesizing 2-halo-4,6-dinitroresorcinol, said process comprising the step of contacting 1,2,3-trihalo-4,6-dinitrobenzene with hydroxide anions in an aqueous solution containing essentially no alkanol under conditions such that a 2-halo-4,6-dinitroresorcinol is formed in yields of at least about 75 percent.

A second aspect of the present invention is a process for synthesizing 4,6-diaminoresorcinol comprising the steps of:
(1) contacting 1,2,3-trihalo-4,6-dinitrobenzene with hydroxide anions in an aqueous solution under conditions such that 2-halo-4,6-dinitroresorcinol is formed; and
(2) contacting the product of step (1) with a hydrogenating agent in the presence of a noble metal hydrogenation catalyst and in the presence of an acid having a higher $pK_a$ than the hydrogen halide of the halogen in the 3-position in an aqueous solution under conditions such that 4,6-diaminoresorcinol or an acid salt thereof is formed.

The processes of the present invention can be used to synthesize 2-halo-4,6-dinitroresorcinol intermediate and 4,6-diaminoresorcinol monomer. The monomer can be used to synthesize polybenzoxazole polymers according to the processes described in U.S. Pat. Nos. 4,533,692 and 4,533,693, which are incorporated herein by reference.

DETAILED DESCRIPTION OF THE INVENTION

The processes of this invention commence with 1,2,3-trihalo-4,6-dinitrobenzene. The halogens are chosen such that those in the 2- and 4-position can be displaced by a hydroxide ion. Each halogen is preferably bromine or chlorine and most preferably chlorine. The 1,2,3-trihalo-4,6-dinitrobenzene can be synthesized by nitration of a 1,2,3-trihalobenzene according to the process described in U.S. Pat. No. 4,766,244, which is incorporated herein by reference.

The 1,2,3-trihalo-4,6-dinitrobenzene is dissolved in an aqueous solution containing essentially no alcohol. The solvent may contain a water-miscible organic solvent other than alcohol, but preferably contains essentially no organic solvent. The amount of water should be sufficient to maintain the 1,2,3-trihalo-4,6-dinitrobenzene in slurry. There is preferably at least about 80 moles of water per mole of organic reagent, more preferably at least about 100 moles of water. The maximum quantity of water is governed primarily by practical considerations. Preferably, no more than about 200 moles of water per mole of organic solvent is used.

The 1,2,3-trihalo-4,6-dinitrobenzene is contacted with hydroxide anions in solution or in slurry. The hydroxide anions are preferably from an alkali metal hydroxide, which may be added to the aqueous solvent before, during or after addition of the 1,2,3-trihalo-4,6-dinitrobenzene. The alkali metal hydroxide is preferably added after the 1,2,3-trihalo-4,6-dinitrobenzene, and more preferably after the reaction mixture has reached about reaction temperature. The alkali metal hydroxide is preferably lithium, sodium or potassium hydroxide, and more preferably sodium hydroxide. The reaction should use at least 4 moles of alkali metal hydroxide per mole of organic reagent. It more preferably uses at least 4.5 moles and most preferably uses at least 6 moles. The reaction preferably uses less than 8 moles of alkali metal hydroxide, more preferably no more than 7 moles.

The process may be carried out at any conditions under which the hydroxide anions will displace halogens in the 1- and 3-positions. The reaction may proceed at reflux (about 105° C.), but is preferably carried out at no more than about 95° C. and more preferably at no more than 90° C. The reaction proceeds only slowly at lower temperatures. It is preferably at least about 60° C., more preferably at least about 75° C. and most preferably at least about 85° C. The pressure may be any under which the reaction mixture remains a stable solution or slurry: it is conveniently about atmospheric pressure. The reaction may be carried out under inert or ambient atmosphere.

The speed of the reaction is dependent upon numerous factors, such as temperature, concentration of hydroxide anions, and the amount of water in the system. Thus, the time of the reaction may vary in a manner familiar to persons of ordinary skill in organic chemistry. Under the most preferred conditions, the reaction is ordinarily completed in about 6 to 8 hours. Under most less preferred conditions, the reaction may take longer, except that reaction at higher than preferred temperature may occur more quickly but with a higher concentration of side products.

During the course of the reaction, the reaction mixture typically commences as a slurry, becomes a solution and then forms another slurry as the reaction goes to completion. It is theorized, without intending to be bound thereby, that the intermediate product, 2,3-dihalo-4,6-dinitrophenol, is substantially more soluble in water than either the 1,2,3-trihalo-4,6-dinitrobenzene reagent or the 2-halo-4,6-dinitroresorcinol product.

The 2-halo-4,6-dinitroresorcinol intermediate may be isolated from the aqueous slurry by filtering and hydrogenated by known means, such as those described in U.S. Pat. Nos. 4,764,263; 4,766,244 and 4,806,688, which are incorporated herein by reference. However, it is preferable to pass the 2-halo-4,6-dinitroresorcinol intermediate in the aqueous slurry directly into an aqueous hydrogenation step. The yield and selectivity of 2-halo-4,6-dinitroresorcinol intermediate from the displacement step is preferably at least about 90 percent, more preferably at least about 95 percent, and most preferably at least about 99 percent, based upon the initial levels of 1,2,3-trihalo-4,6-dinitroresorcinol. These yields and selectivities may be obtained without isolating or purifying the 2,3-dihalo-4,6-dinitrophenol intermediate.

In an aqueous hydrogenation process, the 2-halo-4,6-dinitroresorcinol intermediate is contacted with a hydrogenating agent in the presence of a noble metal hydrogenation catalyst in an aqueous solvent in the presence of an acid which:
(1) is a weaker acid than the hydrogen halide of the halogen atom in the 2-halo-4,6-dinitroresorcinol,
(2) is stable under reaction conditions, and
(3) does not interfere with the functioning of the catalyst,
under conditions such that a 4,6-diaminoresorcinol is formed. The 4,6-diaminoresorcinol typically is formed primarily as an acid salt.

During aqueous hydrogenation, the 2-halo-4,6-dinitroresorcinol is contacted with a hydrogenating agent. The hydrogenating agent may be any known hydrogenating agent which can be used in an aqueous solution, but it is preferably molecular hydrogen. The hydrogenating agent should be present in at least a stoichiometric amount, and is preferably present in a stoichiometric excess over the amount of 2-halo-4,6-dinitroresorcinol.

The contact is made in an aqueous solution or slurry. As previously explained, the 2-halo-4,6-dinitroresorcinols are typically insoluble in aqueous solutions, so the hydrogenation is ordinarily carried out in slurry. The amount of water should be sufficient to dissolve enough hydrogen for a reasonable rate of reaction and to leave the slurry reasonably stirrable. The maximum amount of water is governed primarily by practical considerations. At higher ratios of water to 2-halo-4,6-dinitroresorcinol, the capacity of the reaction equipment is necessarily lower. The slurry preferably contains at most about 0.8 mole of 2-halo-4,6-dinitroresorcinol per liter of water, more preferably at most about 0.7 mole per liter of water and most preferably at most about 0.68 mole per liter of water. If the slurry resulting from the displacement step does not contain sufficient water, then additional water may be added. Alternatively, the 2-halo-4,6-dinitroresorcinol may be isolated, washed and then placed in a new aqueous slurry or solution.

The water may be mixed with organic diluents, such as alkanols and glycols, which are miscible with water and do not interfere with the reaction. The term "organic diluent" does not refer to the acid or the 2-halo-4,6-dinitroresorcinol, but only to organic compounds which function as solvents. The organic diluent preferably makes up a small enough part of the solution to minimize the flame hazard resulting from its presence. The organic diluent preferably makes up no more than 50 percent of the solvent by weight, more preferably no more than 25 percent and more highly preferably no more than 10 percent. The solvent most preferably contains essentially no organic diluent, such that water is the only solvent.

The reaction takes place in the presence of a noble metal hydrogenation catalyst. Suitable noble metals are those known to promote both hydrogenation of nitro groups and hydrogenation of aromatic halides to form aromatic rings and hydrogen halide. Examples of suitable noble metals include gold, silver, platinum, palladium, iridium, rhodium, mercury, ruthenium and osmium. Preferred metals are platinum and palladium, and the most preferred metal is palladium. The catalyst metal may be used in any form which is suitable to catalyze the reaction. For instance, some catalyst metals may be used as a metal oxide, although the catalyst metal is preferably in an unoxidized state. The catalyst may be used in bulk, but is preferably supported by a support, such as carbon. The most preferred catalyst is palladium-on-carbon. Palladium-on-carbon catalysts preferably contain at least about 5 weight percent palladium and more preferably at least about 10 weight percent palladium.

The amount of catalyst used is governed essentially by practical considerations which are familiar to persons of ordinary skill in the art. The reaction takes very long at very low catalyst levels, and the cost of catalyst is uneconomical at high catalyst levels. When the catalyst is 10 percent palladium-on-carbon, the weight percentage of catalyst to 2-halo-4,6-dinitroresorcinol is preferably at least about 1 percent, more preferably at least about 3 percent and most preferably at least about 6 percent. The weight ratio is preferably at most about 15 percent and more preferably at most about 8 percent.

The reaction takes place in the presence of an acid which is a weaker acid than the hydrogen halide of the halogen in the 2-halo-4,6-dinitroresorcinol. For instance, the $pK_a$ of the acid should be no less than $-6.1$ when the halogen of the 2-halo-4,6-dinitroresorcinol is chlorine, because the $pK_a$ of hydrogen chloride is about $-6.1$. The $pK_a$ should be sufficiently low for the acid to stabilize an o-aminohydroxy moiety on the 4,6-diaminoresorcinol product. The $pK_a$ of the acid is preferably greater than $-3$, more preferably at least about 0 and most preferably at least about 1. The $pK_a$ is preferably less than 10, more preferably at most about 4.75 and most preferably at most about 2.75.

The acid must be stable under reaction conditions. For instance, trichloroacetic acid tends to form hydrogen halide under reaction conditions, and is un-suitable suitable for the present process, although trifluoroacetic acid is stable and is suitable.

The acid must also not interfere with the action of the catalyst. Phosphonic acid, hypophosphoric acid, sulfuric acid, sulfonic acid, benzenesulfonic acid and toluenesulfonic acid all interfere with catalyst activity and are inappropriate for the present invention. It is theorized, without intending to be bound, that acids which contain aromatic structures or incomplete octet structures can become adsorbed upon and/or associated with the catalyst metal, thereby obstructing reagents from access to the catalyst.

Examples of suitable acids include phosphoric acid, boric acid, trifluoroacetic acid, fluoroboric acid, methanesulfonic acid, propionic acid, heptanoic acid and acetic acid. Preferred acids are phosphoric acid, methanesulfonic acid, fluoboric acid and trifluoroacetic acid. Trifluoroacetic acid and phosphoric acid are more preferred, and phosphoric acid is most preferred.

The acid should be present in at least a stoichiometric ratio with nitro groups in the 2-halo-4,6-dinitroresorcinol. However, excess acid reduces the solubility of hydrogen in water, thereby lengthening the time needed for the reaction. When the acid is phosphoric acid, the molar ratio of acid to 2-halo-4,6-dinitroresorcinol is preferably at least about 1:1 and more preferably at least about 2:1 at the commencement of the reaction. The molar ratio of acid to 2-halo-4,6-dinitroresorcinol is preferably at most about 10:1, more preferably at most about 5:1 and most preferably at most about 4:1 at the commencement of the reaction. The pH of the slurry varies widely depending upon the acid used, but is preferably between about 1 and 2 for phosphoric acid at the commencement of the reaction. Due to the presence in slurry of hydroxide anions left over from the displacement step, it is ordinarily necessary to add excess acid to obtain the desired levels at the commencement of the hydrogenation.

The hydrogenating agent may be introduced into the slurry by any means effective to achieve a reasonable dispersion. For instance, hydrogen may be sparged into the slurry or introduced into the headspace and dispersed with an entrainment agitator. Good agitation is important to maintain an even dispersion of reagents throughout the system. The temperature of the reaction may be any at which the reaction proceeds and the reagents and products are stable. The maximum temperature achieved during the reaction is preferably at least about 15° C., more preferably at least about 45° C. and most preferably at least about 50° C. It is preferably at most about 100° C., more preferably at most about 65° C. and most preferably at most about 55° C. The reaction should be carried out under a non-oxidizing atmosphere.

Catalyst is preferably removed from the reaction mixture by known means such as filtration.

The product of the aqueous hydrogenation is preferably a 4,6-diaminoresorcinol. The product in solution is protonated, and is more stable with respect to air oxidation if it is precipitated as an acid salt. The product is more susceptible to air oxidation while in solution or wet, so it is preferably precipitated and dried as soon as possible. The acid salts of 4,6-diaminoresorcinol are soluble in warm highly acidic aqueous solvents, but are less soluble in organic or mildly acidic aqueous solutions. Precipitation can be accomplished by any combination of known methods, such as cooling the solution, adding an organic non-solvent or raising the pH of the solution to decrease solubility. Examples of suitable organic non-solvents include alkanols such as methanol, ethanol and propanol. Examples of suitable neutralizing agents which may be used to raise the pH of the solution include alkali metal bicarbonate, ammonium bicarbonate, sodium hydroxide and tertiary amines.

It is theorized that hydrogen halide generated in the reaction tends to displace the weaker acids used in protonating amine groups on the product. If the salt is precipitated without neutralizing acid to raise the pH of the solution, then the precipitated product will be at least in part a hydrogen halide salt. The salt can be precipitated as a completely hydrogen halide salt by adding at least a stoichiometric amount of hydrogen halide acid before precipitation.

On the other hand, it is further theorized that hydrogen halide, as the stronger acid, is neutralized first if a base is added. If non-halide salt such as a phosphate salt is desired, then at least a stoichiometric amount of neutralizing agent may be added to the solution before precipitation, or the solution may be devolitilized according to known procedures to remove hydrogen halide before precipitation. The counterion in the resulting salt is the acid used during reduction.

The selectivity to 4,6-diaminoresorcinol is preferably greater than 90 percent, more preferably at least about 95 percent, and most preferably at least 98 percent based upon the starting 2-halo-4,6-dinitroresorcinol. The product can be purified by known means, such as recrystallization. It can be used to synthesize polybenzoxazole polymers according to the procedures described in U.S. Pat. Nos. 4,533,693; 4,533,692; and 4,772,678, which are incorporated herein by reference.

ILLUSTRATIVE EMBODIMENTS

The following examples are given to illustrate the invention and should not be interpreted as limiting it in any way. Unless stated otherwise, all parts and percentages are given by weight.

EXAMPLE 1

A mixture of 54.3 g of 1,2,3-trichloro-4,6-dinitrobenzene and 336 g of water is heated with constant agitation. When the temperature reaches 35° C., 48 g of a 50 percent caustic soda solution is added in one portion. Heating is continued to 75° C., and the mixture is maintained at 75° C. to 80° C. with stirring for about 18 hours. The reaction mixture is cooled to room temperature and neutralized with concentrated hydrochloric acid. The product is filtered and dried. Infrared spectroscopy (IR) shows the product to be 2-chloro-4,6-dinitroresorcinol, and gas chromatography (GC) shows it to be 99.3 percent pure. The recovered yield is 92 percent.

EXAMPLE 2

The procedure of Example 1 is repeated several times using the amounts of 1,2,3-trichloro-4,6-dinitrobenzene (TCDNB), water and caustic soda shown in Table 1. (Caustic soda is added in a 50 weight percent aqueous solution, but the quantity shown is the quantity of caustic soda alone.) The TCDNB is mixed with water in a 1000 ml resin kettle equipped with a double-paddle stirrer, a thermometer and a reflux condenser. The stirrer is set for 1000 rpm. The reaction mixture is heated. The caustic soda solution is added in each case when the temperature reaches about 70° C. The temperature of the reaction is raised to and maintained at about the temperature shown in Table 1. Samples are analyzed by GC at regular intervals throughout the reaction. Each reaction is continued for 6 hours and then terminated, except that the reaction of sample 15 is terminated after 3 hours when GC shows that the reaction is completed. The GC analysis shows that those samples having an asterisk (*) were not complete when the reaction was terminated after 6 hours. Samples without an asterisk yield 2-chloro-4,6-dinitroresorcinol with at least 90 percent purity and a 75 percent yield. The major impurity in samples with an asterisk is unconverted 2,3-dichloro-4,6-dinitrophenol.

TABLE 1

| Sample No. | TCDNB (g) | Water (g) | Caustic (g) | Temp. (°C.) |
|---|---|---|---|---|
| 1 | 54.3 | 360 | 48.0 | 85 |
| 2* | 57.0 | 378 | 32.8 | 85 |
| 3* | 62.5 | 332 | 69.0 | 75 |
| 4* | 66.5 | 353 | 44.1 | 75 |
| 5* | 46.1 | 367 | 51.0 | 75 |
| 6* | 54.3 | 360 | 48.0 | 61 |
| 7* | 62.5 | 331 | 40.0 | 85 |
| 8* | 47.5 | 378 | 31.5 | 75 |
| 9 | 62.5 | 332 | 69.0 | 95 |
| 10 | 65.2 | 346 | 43.2 | 95 |
| 11 | 44.8 | 381 | 39.6 | 85 |
| 12 | 54.3 | 360 | 48.0 | 85 |
| 13 | 70.6 | 336 | 62.4 | 85 |
| 14 | 54.3 | 360 | 48.0 | 85 |
| 15 | 54.3 | 360 | 48.0 | 99 |
| 16 | 46.1 | 316 | 102 | 95 |
| 17 | 47.5 | 341 | 63 | 95 |
| 18 | 54.3 | 360 | 48 | 71 |

What is claimed is:

1. A process for synthesizing 2-halo-4,6-dinitroresorcinol, said process comprising the step of contacting a 1,2,3-trihalo-4,6-dinitrobenzene with hydroxide anions in an aqueous solution or slurry containing essentially no alkanol under conditions such that a 2-halo-4,6-dinitroresorcinol is formed in yields of at least about 75 percent.

2. The process of claim 1 wherein each halogen on the 1,2,3-trihalo-4,6-dinitrobenzene is individually chlorine or bromine.

3. The process of claim 2 wherein each halogen on the 1,2,3-trihalo-4,6-dinitrobenzene is chlorine.

4. The process of claim 1 wherein the hydroxide anions are the product of an alkali metal hydroxide added to the reaction mixture or the aqueous solvent.

5. The process of claim 4 wherein the alkali metal hydroxide is lithium, sodium or potassium hydroxide.

6. The process of claim 4 wherein the alkali metal hydroxide is sodium hydroxide.

7. The process of claim 4 wherein the reaction mixture contains at least about 4 moles of alkali metal hydroxide per mole of 1,2,3-trihalo-4,6-dinitrobenzene.

8. The process of claim 4 wherein the reaction mixture contains between about 4.5 and 8 moles of alkali metal hydroxide per mole of 1,2,3-trihalo-4,6-dinitrobenzene.

9. The process of claim 4 wherein the alkali metal hydroxide is added to a slurry containing water and 1,2,3-trihalo-4,6-dinitrobenzene.

10. The process of claim 1 wherein the reaction mixture contains at least about 80 moles of water per mole of 1,2,3-trihalo-4,6-dinitrobenzene.

11. The process of claim 1 wherein the reaction mixture contains at least about 100 moles of water per mole of 1,2,3-trihalo-4,6-dinitrobenzene.

12. The process of claim 1 wherein the temperature of the reaction is between about 60° C. and reflux.

13. A process for synthesizing 2-halo-4,6-dinitroresorcinol, said process comprising the step of contacting a 1,2,3-trihalo-4,6-dinitrobenzene with an alkali metal hydroxide in an aqueous solution or slurry containing at least about 80 moles of water per mole of 1,2,3-trihalo-4,6-dinitrobenzene at a temperature of at least about 70° C. under conditions such that a 2-halo-4,6-dinitroresorcinol is formed in yields of at least about 75 percent.

14. The process of claim 13 wherein the 1,2,3-trihalo-4,6-dinitrobenzene is 1,2,3-trichloro-4,6-dinitrobenzene.

15. The process of claim 14 wherein the reaction mixture contains between 4 and 8 moles of alkali metal hydroxide per mole of 1,2,3-trichloro-4,6-dinitrobenzene.

16. The process of claim 15 wherein the temperature of the reaction is between about 75° C. and 95° C.

17. The process of claim 16 wherein the reaction mixture contains between 100 and 200 moles of water per mole of 1,2,3-trihalo-4,6-dinitrobenzene.

18. The process of claim 17 wherein the alkali metal hydroxide is added to a slurry containing the water and the 1,2,3-trichloro-4,6-dinitrobenzene.

19. The process of claim 18 wherein the reaction mixture contains between 4.5 and 7 moles of alkali metal hydroxide.

20. The process of claim 19 wherein the alkali metal hydroxide is lithium, sodium or potassium hydroxide.

* * * * *